(12) United States Patent
Ichikawa et al.

(10) Patent No.: US 12,318,518 B2
(45) Date of Patent: Jun. 3, 2025

(54) BLOOD PURIFICATION DEVICE

(71) Applicant: Nikkiso Company Limited, Tokyo (JP)

(72) Inventors: Takeshi Ichikawa, Shizuoka (JP);
Shinya Hasegawa, Shizuoka (JP);
Masamichi Sakamaki, Shizuoka (JP);
Kunihiko Akita, Shizuoka (JP);
Hiroaki Mochizuki, Tokyo (JP)

(73) Assignee: Nikkiso Company Limited, Tokyo (JP)

( * ) Notice: Subject to any disclaimer, the term of this patent is extended or adjusted under 35 U.S.C. 154(b) by 483 days.

(21) Appl. No.: 17/610,295

(22) PCT Filed: May 1, 2020

(86) PCT No.: PCT/JP2020/018464
§ 371 (c)(1),
(2) Date: Nov. 10, 2021

(87) PCT Pub. No.: WO2020/235340
PCT Pub. Date: Nov. 26, 2020

(65) Prior Publication Data
US 2022/0211924 A1 Jul. 7, 2022

(30) Foreign Application Priority Data

May 23, 2019 (JP) .................................. 2019-097205
May 31, 2019 (JP) .................................. 2019-102813

(51) Int. Cl.
*A61M 1/16* (2006.01)

(52) U.S. Cl.
CPC ........ *A61M 1/1607* (2014.02); *A61M 1/1601* (2014.02); *A61M 1/1657* (2022.05); *A61M 2205/18* (2013.01)

(58) Field of Classification Search
CPC ........ A61M 1/16; A61M 1/36; A61M 1/1607; A61M 1/1657; A61M 1/168;
(Continued)

(56) References Cited

U.S. PATENT DOCUMENTS 6,156,002 A * 12/2000 Polaschegg ........... A61M 1/165
604/4.01
9,233,199 B2 1/2016 Krause et al.

FOREIGN PATENT DOCUMENTS

CN 103721306 A 4/2014
CN 204033882 U 12/2014
(Continued)

OTHER PUBLICATIONS

European Search Report for Application No. 20810584.1, dated Dec. 19, 2022, 7 pgs.
(Continued)

*Primary Examiner* — Richard C Gurtowski
(74) *Attorney, Agent, or Firm* — Young Basile Hanlon & MacFarlane, P.C.

(57) ABSTRACT

A blood purification device for blood purification therapy performed through a blood purifier, the blood purification device includes piping; a plurality of sensors of different detection types that are provided on the piping; and a liquid chemical identification unit that identifies a type of a cleaning/disinfection liquid chemical flowing through the piping by using the plurality of sensors. The liquid chemical identification unit is configured to be able to identify types of the liquid chemicals of at least not less than the number of the plurality of sensors by using the plurality of sensors.

6 Claims, 3 Drawing Sheets

(58) Field of Classification Search
CPC ...... A61M 2205/18; A61M 2205/3306; A61M 2205/3317; A61M 2205/3324; A61M 60/37; A61M 60/11; A61M 60/45; A61M 1/1601

See application file for complete search history.

(56) References Cited

FOREIGN PATENT DOCUMENTS

| | | |
|---|---|---|
| CN | 107405440 A | 11/2017 |
| CN | 109689126 A | 4/2019 |
| JP | H03101956 U | 10/1991 |
| JP | H10-5764 A | 1/1998 |
| JP | 2010-207 A | 1/2010 |
| JP | 2014-097197 A | 5/2014 |
| WO | 2012/169527 A1 | 12/2012 |

OTHER PUBLICATIONS

Japanese Office Action for Application No. 2019-102813, dated Nov. 8, 2022, with English translation, 7 pages.
Chinese Office Action for Application No. 202080037750.X dated Jan. 11, 2024, with English translation, 14 pgs.
International Search Report for Application No. PCT/JP2020/018464, dated Jul. 14, 2020.
Chinese Office Action for Application No. 202080037750.X, dated Jul. 30, 2024, with English translation, 16 pgs.
European Search Report for Application No. 20810584.1, dated Dec. 17, 2024, 6 pgs.

* cited by examiner

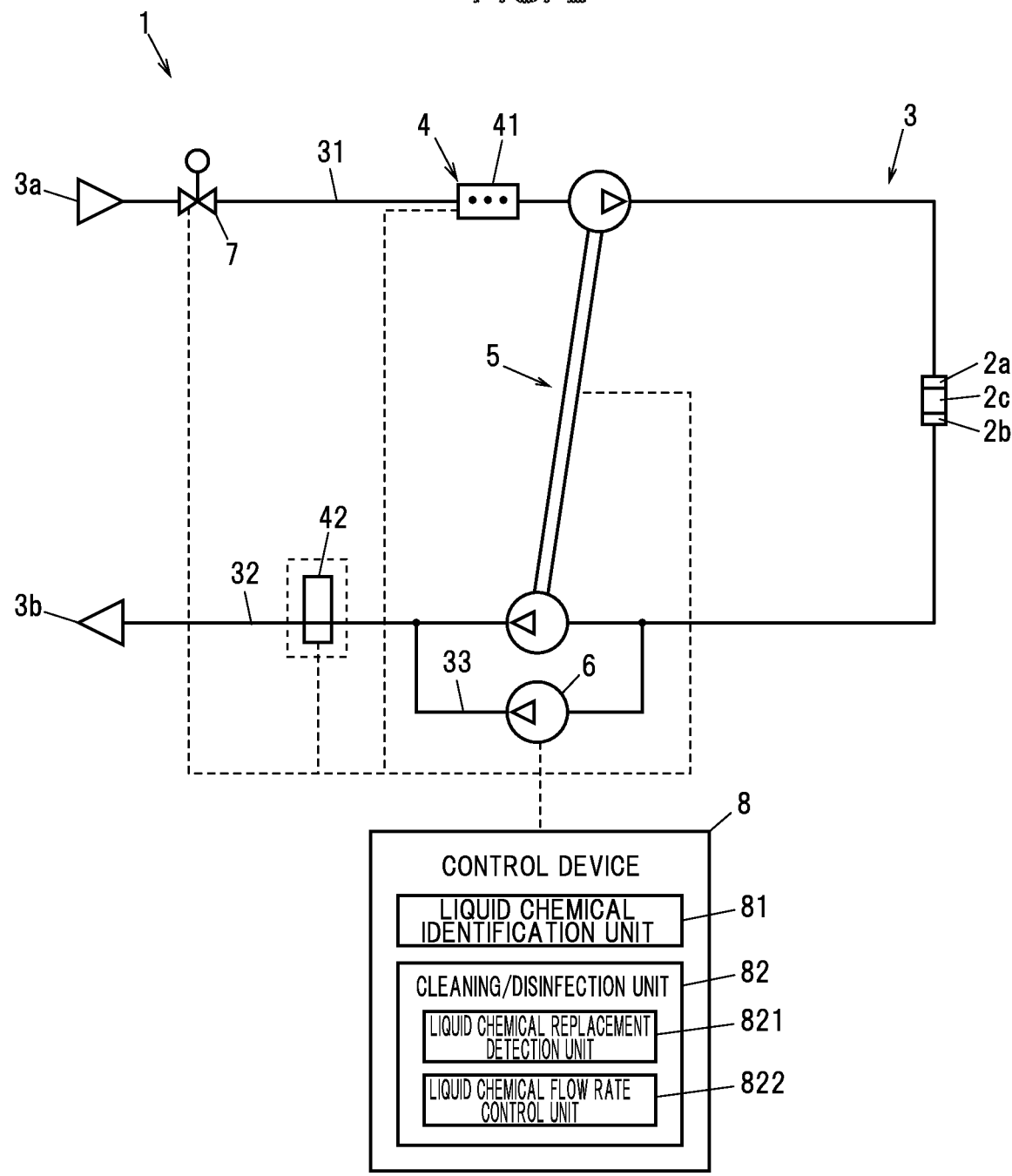

BLOOD PURIFICATION DEVICE

CROSS-REFERENCE TO RELATED APPLICATION(S)

This application is a continuation of International Application No. PCT/JP2020/018464, filed on May 1, 2020, which claims priority to Japanese Application Nos. 2019-097205, filed on May 23, 2019 and 2019-102813, filed May 31, 2019, the entire disclosures of which are hereby incorporated by reference.

TECHNICAL FIELD

The invention relates to a blood purification device.

BACKGROUND ART

For blood purification devices, a cleaning/disinfecting process for cleaning/disinfecting the inside of piping is performed after blood purification therapy. In the cleaning/disinfecting process, a cleaning/disinfection liquid chemical is introduced into the piping and the inside of the piping is cleaned/disinfected (see, e.g., Patent Document 1).

CITATION LIST

Patent Literature

Patent Document 1: J P2014-097197A

SUMMARY OF INVENTION

Technical Problem

In the cleaning/disinfecting process, different liquid chemicals are used depending on how dirty inside the piping is or how frequently the device is used, etc. Time required for cleaning/disinfection and the control details, etc., are different when using different liquid chemicals. Therefore, if, e.g., a wrong liquid chemical is used, cleaning/disinfection may be performed excessively which causes the liquid chemical to be wasted, or cleaning/disinfection may not be sufficiently performed which adversely affects the subsequent therapy.

For example, a blood purification device into which a liquid chemical is introduced from an external device could receive data of the type of liquid chemical used from the external device by communication, etc. However, even in such a case, to further increase safety, it is desired that each blood purification device identifies the type of the actually supplied liquid chemical and determines whether the correct liquid chemical is supplied.

Therefore, it is an object of the invention to provide a blood purification device that is capable of identifying types of cleaning/disinfection liquid chemicals and allows an appropriate cleaning/disinfecting process according to the type of liquid chemical to be performed.

Solution To Problem

To solve the problem mentioned above, the invention according to variation 1 provides a blood purification device for blood purification therapy performed through a blood purifier, the blood purification device comprising:
piping;
a plurality of sensors of different detection types that are provided on the piping; and
a liquid chemical identification unit that identifies a type of a cleaning/disinfection liquid chemical flowing through the piping by using the plurality of sensors,
wherein the liquid chemical identification unit is configured to be able to identify types of the liquid chemicals of at least not less than the number of the plurality of sensors by using the plurality of sensors.

The invention according to variation 2 is the blood purification device according to variation 1, wherein the liquid chemical identification unit selects all or part of the plurality of sensors according to the type of the liquid chemical which should be used for cleaning/disinfection and, based on detection results from the selected all or part of sensors, identifies whether or not it is a liquid chemical which should be used for the cleaning/disinfection.

The invention according to variation 3 is the blood purification device according to variation 1 or 2, wherein the liquid chemical identification unit is configured to be able to identify types of the liquid chemicals of more than the number of the plurality of sensors based on a combination of the detection results from the plurality of sensors.

The invention according to variation 4 is the blood purification device according to any one of variations 1 to 3, further comprising:
a cleaning/disinfection control unit to detect whether the piping is filled with the cleaning/disinfection liquid chemical at the time of cleaning/disinfecting the piping, based on a detection result from at least one of the plurality of sensors.

The invention according to variation 5 is the blood purification device according to variation 4, wherein the cleaning/disinfection control unit is configured to be able to detect whether a dialysate or the liquid chemical in the piping has been replaced with dialysis water, based on a detection result from at least one of the plurality of sensors.

The invention according to variation 6 is the blood purification device according to any one of variations 1 to 5, wherein the plurality of sensors comprise a conductivity sensor to measure conductivity of a liquid flowing through the piping, and an absorbance sensor to measure absorption of ultraviolet light by the liquid flowing through the piping.

The invention according to variation 7 is the blood purification device according to variation 6, wherein the liquid chemical identification unit identifies a type of the liquid chemical by comparing a threshold for a detection value of the conductivity sensor and a threshold for a detection value of the absorbance sensor, which are set for each type of the liquid chemical, with the detection values of the conductivity sensor and the absorbance sensor.

According to the invention of variations 1 and 3, it is possible to identify the type of the cleaning/disinfection liquid chemical and possible to perform an appropriate cleaning/disinfecting process according to the type of the liquid chemical.

According to the invention of variation 2, it is possible to identify whether or not the liquid chemical used currently is a liquid chemical which should be used for cleaning/disinfection.

According to the invention of variation 4, it is possible to detect whether the piping is filled with the cleaning/disinfection liquid chemical, and possible to perform an appropriate cleaning/disinfecting process.

According to the invention of variation 5, it is possible to suppress insufficient cleaning/disinfection due to the dialysate remaining after pre-cleaning or problems in blood purification therapy due to the liquid chemical remaining after post-cleaning.

According to the invention of variation 6, since the sensors respectively detect conductivity and absorbance, it is possible to detect liquid chemicals having different compositions and possible to identify more types of cleaning/disinfection liquid chemicals.

According to the invention of variation 7, it is possible to identify an acid cleaning solution, a peracetic acid-based disinfectant and a hypochlorite disinfectant, which are typical liquid chemicals used for the cleaning/disinfecting process.

BRIEF DESCRIPTION OF DRAWINGS

FIG. 2 is a schematic configuration diagram illustrating the blood purification device.

DESCRIPTION OF EMBODIMENTS

Embodiment

An embodiment of the invention will be described below in conjunction with the appended drawings.

Figure 1:
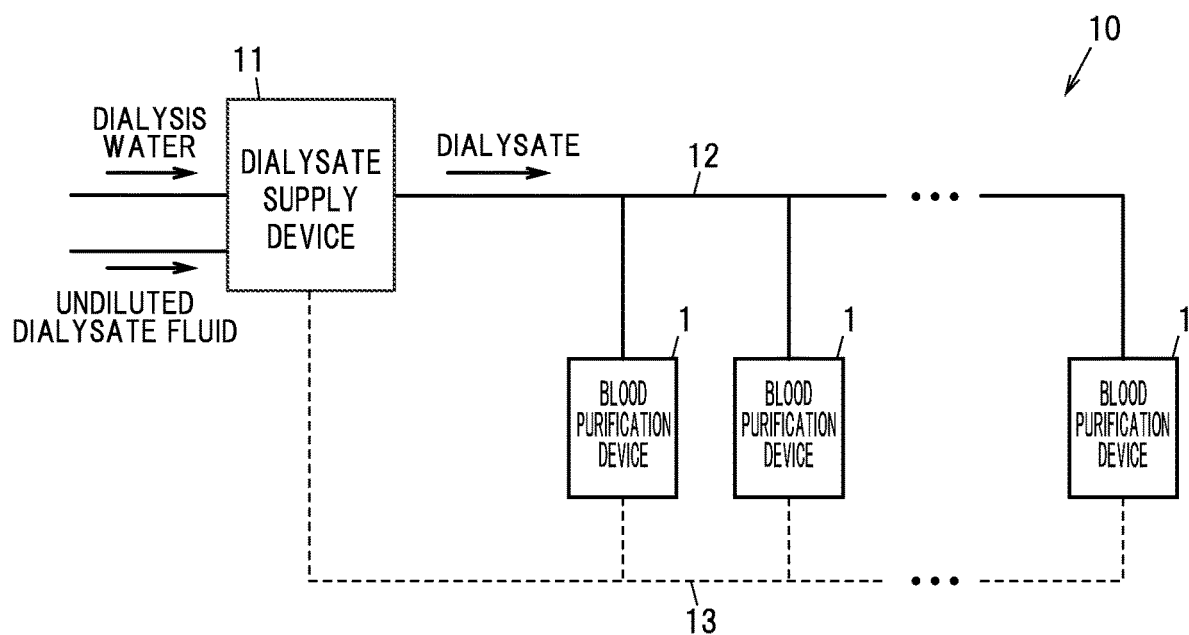
FIG. 1 is a schematic configuration diagram illustrating a blood purification system using blood purification devices in an embodiment of the present invention.

FIG. 1 is a schematic configuration diagram illustrating a blood purification system using blood purification devices in the present embodiment. As shown in FIG. 1, a blood purification system 10 includes a dialysate supply device 11 and plural blood purification devices 1.

The dialysate supply device 11 prepares a dialysate with a predetermined concentration using dialysis water supplied from a water treatment device (not shown) and an undiluted dialysate fluid supplied from a dissolving device (not shown), and supplies the prepared dialysate to each blood purification device 1. The dialysate prepared by the dialysate supply device 11 is supplied to each blood purification device 1 via a dialysate supply line 12.

Each blood purification device 1 is connected to a blood purifier (a dialyzer, not shown) for providing blood purification therapy (dialysis therapy) to a patient and supplies the dialysate supplied from the dialysate supply device 11 to the blood purifier. The details of the blood purification device 1 will be described later.

The blood purification system 10 is configured such that the dialysate supply device 11 can communicate with each blood purification device 1 via a signal line 13. The dialysate supply device 11 can detect an operating status of each blood purification device 1 and control each blood purification device 1. The form of communication between the dialysate supply device 11 and each blood purification device 1 is not limited thereto and may be, e.g., wireless communication instead of wired communication.

In the blood purification system 10, a cleaning/disinfecting process for cleaning/disinfecting the inside of piping is performed after blood purification therapy. The cleaning/disinfecting process here includes a case where only cleaning is performed, a case where only disinfection is performed, and a case where both cleaning and disinfection are performed. When performing the cleaning/disinfecting process, the dialysate supply device 11 prepares a liquid chemical used for cleaning/disinfection and supplies the prepared liquid chemical to each blood purification device 1 via the dialysate supply line 12. The dialysate supply device 11 also has a function of notifying each blood purification device 1 of the type, etc., of liquid chemical to be used when performing the cleaning/disinfecting process. When a worker operates the dialysate supply device 11 to start the cleaning/disinfecting process, the cleaning/disinfecting process for the dialysate supply device 11 and each blood purification device 1 is automatically performed according to a program preset in the dialysate supply device 11.

(Blood Purification Device 1)

FIG. 2 is a schematic configuration diagram illustrating the blood purification device 1. FIG. 2 schematically shows piping arrangement during cleaning/disinfection. As shown in FIG. 2, the blood purification device 1 has a pair of connectors 2a, 2b to which the blood purifier (not shown) is connected. During cleaning/disinfection, the two connectors 2a, 2b are connected via a bypass connector 2c.

Piping 3 inside the blood purification device 1 has a supply-side flow path 31 including a liquid supply port 3a connected to the dialysate supply line 12 and the connector 2a, and a discharge-side flow path 32 including the other connector 2b and a liquid discharge port 3b.

The blood purification device 1 also has a dual pump 5 which is configured to operate so that an amount of liquid supplied to the blood purifier and an amount of liquid discharged from the blood purifier are mechanically equivalent. In the present embodiment, the dual pump 5 is used to control a flow rate of the liquid flowing through the piping 3. In addition, a removed water flow path 33 is provided on the discharge-side flow path 32 so as to bypass the dual pump 5, and a water removal pump 6 to control an amount of water removed from blood is provided on the removed water flow path 33. In addition, a liquid supply valve 7 composed of a solenoid valve capable of shutting off liquid supply is provided on the supply-side flow path 31. The configuration diagram in FIG. 2 is simplified, and a flow path for bypassing each part, a solenoid valve, a filter unit, a pressure sensor for measuring liquid pressure, a temperature sensor for measuring liquid temperature, etc., may be appropriately provided.

The blood purification device 1 also includes a control device 8 that controls the dual pump 5, the water removal pump 6, the liquid supply valve 7, etc. The control device 8 controls each part during blood purification therapy or during cleaning/disinfection.

The blood purification device 1 in the present embodiment includes plural sensors of different detection types provided on the piping 3 inside the device, and a liquid chemical identification unit 81 that identifies a type of cleaning/disinfection liquid chemical flowing through the piping 3 by using the plural sensors 4.

The plural sensors 4 are provided on the piping 3 and can detect that a cleaning/disinfection liquid chemical is flowing through the piping 3. In the present embodiment, these plural sensors 4 are used to determine the type of the cleaning/disinfection liquid chemical. In the present embodiment, a conductivity sensor 41 to measure conductivity of a liquid flowing through the piping 3 and an absorbance sensor 42 to measure absorption of ultraviolet light in the 280-nm band by the liquid flowing through the piping 3 are used as the plural sensors 4. However, the sensors 4 are not limited thereto, and, e.g., a pH sensor to measure pH of the liquid flowing through the pipe 3, etc., may be included.

The conductivity sensor 41 is used to monitor a dialysate concentration during blood purification therapy and is provided on the supply-side flow path 31. When the dialysate concentration exceeds a threshold during blood purification therapy, an alarm is issued and is visually or audibly notified via a user interface, such as a display unit (not shown). Meanwhile, the absorbance sensor 42 is used to measure absorbance of waste liquid from the blood purifier, detect an amount of urea nitrogen contained in the waste liquid and monitor the progress of dialysis during blood purification therapy, and is provided on the discharge-side flow path 32. That is, in the present embodiment, the conductivity sensor 41 and the absorbance sensor 42, which are conventionally used in blood purification therapy, are used for a different purpose and are used to determine the type of cleaning/disinfection liquid chemical. As a result, it is not necessary to separately provide a sensor for determining the type of cleaning/disinfection liquid chemical, the system configuration is simplified, and it is possible to reduce the cost.

Typical liquid chemicals used for cleaning/disinfection include an acid cleaning solution, a peracetic acid-based disinfectant and a hypochlorite disinfectant. Of those, the acid cleaning solution and the hypochlorite disinfectant have different conductivities from that of the dialysis water and thus can be detected by the conductivity sensor 41. Meanwhile, of the liquid chemicals mentioned above, the peracetic acid-based disinfectant and the hypochlorite disinfectant exhibit different UV absorbances (ultraviolet light in the 280-nm band) from that of the dialysis water and thus can be detected by the absorbance sensor 42. As such, in the present embodiment, two or more types (three types in this example) of liquid chemicals can be detected by using two sensors 4.

Since conductivity detected by the conductivity sensor 41 and absorbance detected by the absorbance sensor 42 depend on the concentration of the liquid chemical flowing through the piping 3, the concentration of the liquid chemical can also be detected by detecting conductivity or absorbance. That is, in the present embodiment, the sensors 4 are configured to be able to detect the concentration of the liquid chemical flowing through the piping 3.

The liquid chemical identification unit 81 is mounted on the control device 8 and is realized by appropriately combining an arithmetic element such as CPU, a storage device such as memory, a software, and an interface, etc. The liquid chemical identification unit 81 is configured to be able to identify types of the liquid chemicals of at least not less than the number of the sensors 4 based on detection results from the plural sensors 4. In the present embodiment, the liquid chemical identification unit 81 is configured to be able to identify types of the liquid chemicals of more than the number of the plural sensors 4 based on a combination of the detection results from the plural sensors 4.

In more particular, the liquid chemical identification unit 81 identifies the type of the liquid chemical by comparing a threshold (within a reference value range) for a detection value of the conductivity sensor 41 and a threshold (within a reference value range) for a detection value of the absorbance sensor 42, which are set for each type of liquid chemical, with the detection values of the conductivity sensor 41 and the absorbance sensor 42. For example, when the detection values of the conductivity sensor 41 and the absorbance sensor 42 are respectively within the reference value ranges for an acid cleaning solution, it is identified that the liquid chemical is the acid cleaning solution. However, it is not limited thereto. Based the detection results from the conductivity sensor 41 and the absorbance sensor 42, the liquid chemical identification unit 81 may identify that the liquid chemical is the acid cleaning solution when only the detection value of the conductivity sensor 41 changes as compared to measurement result of the dialysis water (when the amount of change is not less than a predetermined threshold), the liquid chemical is the peracetic acid-based disinfectant when only the detection value of the absorbance sensor 42 changes (when the amount of change is not less than a predetermined threshold), and the liquid chemical is the hypochlorite disinfectant when the detection values of the conductivity sensor 41 and the absorbance sensor 42 both change (when the amount of change is not less than a predetermined threshold).

In the present embodiment, the control device 8 is configured to communicate with the dialysate supply device 11 and acquire information indicating the liquid chemical used in the cleaning/disinfecting process from the dialysate supply device 11. The liquid chemical identification unit 81 is configured to specify the liquid chemical based on the acquired information indicating the liquid chemical and select the sensor corresponding to the specified liquid chemical from the plural sensors 4.

As such, in the present embodiment, the liquid chemical identification unit 81 selects all or part of the plural sensors 4 according to the type of the liquid chemical which should be used for cleaning/disinfection. The liquid chemical identification unit 81 is also configured to identify whether or not the liquid chemical used currently is a liquid chemical which should be used for cleaning/disinfection, based on the detection results from the selected all or part of sensors 4. The reference value ranges mentioned above are set within a range in which the type of the liquid chemical can be identified. Therefore, by determining whether or not the concentration of the liquid chemical is within the reference value range, it is possible to determine whether or not the type of the liquid chemical is appropriate in addition to whether or not the concentration of the liquid chemical is appropriate. As a result, it is possible to avoid cleaning/disinfection with an inappropriate type of liquid chemical even when a user puts a wrong type of liquid chemical instead of the liquid chemical which should be supplied and a liquid chemical of a different type from the controlled liquid chemical is sent from the dialysate supply device 11 due to the control.

The blood purification device 1 also includes a cleaning/disinfection control unit 82 to cause the cleaning/disinfection liquid chemical to flow through the piping 3 inside the device and perform the cleaning/disinfecting process for the piping 3. The cleaning/disinfection control unit 82 performs the cleaning/disinfecting process according to the instruction from the dialysate supply device 11. The cleaning/disinfection control unit 82 is mounted on the control device 8 and is realized by appropriately combining an arithmetic element such as CPU, a storage device such as memory, a software, and an interface, etc. The cleaning/disinfection control unit 82 has a liquid chemical replacement detection unit 821 and a liquid chemical flow rate control unit 822.

The liquid chemical replacement detection unit 821 is configured to detect, during cleaning/disinfecting the piping 3, that the piping 3 is filled with the cleaning/disinfection liquid chemical (the other liquid is replaced with the liquid chemical), based on the detection result from at least one sensor 4. The liquid chemical replacement detection unit 821 uses the detection result from the sensor 4 corresponding to the liquid chemical identified by the liquid chemical identification unit 81, compares the detection value of the sensor 4 with the threshold corresponding to the identified liquid chemical, and thereby detects that the liquid chemical is flowing through the piping 3 at a position where the sensor 4 is provided. In other words, when the concentration of the liquid chemical detected by the sensor 4 exceeds a predetermined reference value, the liquid chemical replacement detection unit 821 detects that the liquid chemical is flowing through the piping 3 at the position where the sensor 4 is provided.

When the liquid chemical identification unit 81 identifies that the liquid chemical used is, e.g., an acid cleaning solution, the liquid chemical replacement detection unit 821 compares the detection value of the conductivity sensor 41 with a preset threshold for the acid cleaning solution and detects that the liquid chemical is flowing through the piping 3 at the position where the conductivity sensor 41 is provided. In case of the hypochlorite disinfectant, the flow of the liquid chemical may be detected by using only one of the conductivity sensor 41 and the absorbance sensor 42 or the flow of the liquid chemical may be detected by using both sensors 41, 42.

During cleaning/disinfection, the entire piping 3 including the downstream side of the sensor 4 need to be filled with the liquid chemical. Therefore, when a delay time preset according to a piping capacity of the piping 3 on the downstream side of the sensor 4 used to detect flow of a liquid chemical has elapsed after detection of the flow of the liquid chemical, the liquid chemical replacement detection unit 821 detects that the piping 3 is filled with the cleaning/disinfection liquid chemical. For example, in case that the conductivity sensor 41 detects the liquid chemical, the delay time is set longer since it is arranged on the upstream side of the absorbance sensor 42 in a direction of sending the liquid chemical.

As such, the threshold (the reference value of the concentration) for detection of the flow of the liquid chemical and length of the delay time are different depending on the liquid chemical to be used. By providing the liquid chemical identification unit 81, it is possible to perform an appropriate cleaning/disinfecting process according to the type of the liquid chemical actually used even when there is a human error such as, e.g., using a liquid chemical which is different from the intended liquid chemical. The liquid chemical identification unit 81 may be configured to issue an alarm by, e.g., sending an alert signal to the dialysate supply device 11 when the liquid chemical notified by the dialysate supply device 11 is different from the identified liquid chemical.

When the liquid chemical replacement detection unit 821 detects that the piping 3 is filled with the liquid chemical, the liquid chemical flow rate control unit 822 performs a process of reducing a flow rate of the liquid chemical as compared with that before the detection. In the present embodiment, the liquid chemical flow rate control unit 822 is configured to control the flow rate of the liquid chemical by controlling the dual pump 5.

As a result of study, the present inventors found that a cleaning/disinfecting effect is dominant during when the liquid chemical is in contact with the piping 3 and a sufficient cleaning/disinfecting effect is obtained even if the flow rate of the liquid chemical is reduced. However, to efficiently perform the cleaning/disinfecting process in a short time, the flow rate of the liquid chemical is desirably as high as possible until the piping 3 is filled with the liquid chemical. Therefore, in the present embodiment, the flow rate of the liquid chemical is reduced after the piping 3 is filled with the liquid chemical, thereby reducing the use amount of the liquid chemical while maintaining the sufficient cleaning/disinfecting effect.

To shorten the time required for the cleaning/disinfecting process, the flow rate of the liquid chemical before the piping 3 is filled with the liquid chemical is desirably as high as possible. Meanwhile, to reduce the use amount of the liquid chemical, the flow rate of the liquid chemical after the piping 3 is filled with the liquid chemical is desirably as low as possible. Thus, the flow rate of the liquid chemical after the piping 3 is filled with the liquid chemical is desirably not more than ½, more preferably not more than ¼, of the flow rate of the liquid chemical before the piping 3 is filled with the liquid chemical. In this regard, however, if the flow rate of the liquid chemical after the piping 3 is filled with the liquid chemical is excessively reduced, dirt, etc., is less likely to be washed away and the cleaning/disinfecting effect may decrease. Therefore, the flow rate of the liquid chemical after the piping 3 is filled with the liquid chemical should be set taking into account the piping capacity, etc., so that the cleaning/disinfecting effect can be maintained.

The cleaning/disinfection control unit 82 is configured to determine that cleaning/disinfection with the liquid chemical has been finished, to stop the dual pump 5 and to proceed to the next step (a post-cleaning (described later), etc.), when a predetermined disinfection/cleaning time has elapsed after detecting that the piping 3 is filled with the liquid chemical. In this regard, after the disinfection/cleaning time has elapsed, the cleaning/disinfecting process may be finished in the state in which the dual pump 5 is stopped and the cleaning/disinfection liquid chemical is enclosed in the piping 3. The disinfection/cleaning time may be set for each liquid chemical to be used. To sufficiently clean/disinfect the solenoid valve such as the liquid supply valve 7, the cleaning/disinfection control unit 82 should control to open and close the solenoid valve at predetermined time intervals from when detecting that the piping 3 is filled with the liquid chemical to when the predetermined disinfection/cleaning time elapses.

When the concentration of the liquid chemical decreases for some reason (e.g., insufficient liquid chemical, etc.) before the disinfection/cleaning time elapses after detecting that the piping 3 is filled with the liquid chemical, a sufficient cleaning/disinfecting effect may not be obtained. Thus, the cleaning/disinfection control unit 82 may be configured to increase the flow rate of the liquid chemical by the liquid chemical flow rate control unit 822 and detect whether the piping 3 is filled with the liquid chemical by the liquid chemical replacement detection unit 821 again when the liquid chemical replacement detection unit 821 detects that the concentration of the liquid chemical is below the reference value (when the detection value of the sensor 4 is below the threshold) before the disinfection/cleaning time elapses after detecting that the piping 3 is filled with the liquid chemical. As a result, even if the concentration of the liquid chemical decreases during cleaning/disinfection for some reason, it is possible to prevent the process from being finished without sufficient cleaning/disinfection. In addition, the cleaning/disinfection control unit 82 may be configured to issue an alarm by, e.g., sending an alert signal to the dialysate supply device 11 when a decrease in the concentration of the liquid chemical is detected.

Figure 3A:
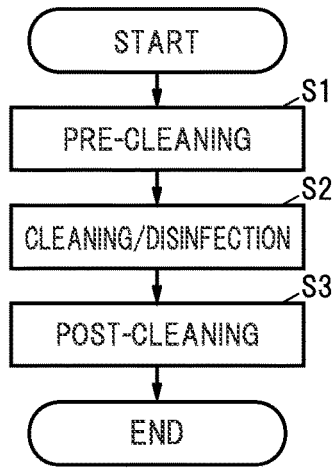
FIG. 3A is a flowchart showing a cleaning/sterilization process.

Now, the procedure of the cleaning/disinfecting process will be described using FIGS. 3A and 3B. When the cleaning/disinfecting process is started, the dialysate for blood purification therapy remains in the piping 3. Thus, in the cleaning/disinfecting process, pre-cleaning for replacing the dialysate in the piping 3 with the dialysis water is firstly performed in Step S1, as shown in FIG. 3A. After that, cleaning/disinfection using the cleaning/disinfection liquid chemical is performed in Step S2. After that, post-cleaning for replacing the liquid chemical in the piping 3 with the dialysis water is performed in Step S3. Alternatively, the cleaning/disinfecting process may be finished while leaving the liquid chemical enclosed in the piping 3 as described above, without performing the post-cleaning in Step S3. In this case, the post-cleaning is performed before the next blood purification therapy.

As described previously, the conductivity sensor 41 used as the sensor 4 can detect the concentration of the dialysate and the absorbance sensor 42 can detect the concentration of urea nitrogen in the waste liquid. Thus, by monitoring the detection values of the conductivity sensor 41 and the absorbance sensor 42, it is possible to detect whether the dialysate (including the waste liquid) in the piping 3 has been replaced with the dialysis water at the time of the pre-cleaning. Therefore, the cleaning/disinfection control unit 82 in the present embodiment is configured to be able to detect whether the dialysate in the piping 3 has been replaced with dialysis water at the time of the pre-cleaning in Step S1, based on the detection result from at least one sensor 4. The cleaning/disinfection control unit 82 is configured to determine whether the inside of the piping 3 has been replaced with the dialysis water based on the detection result from the sensor 4, and proceed to cleaning/disinfection in Step S2 when it is determined that the inside of the piping 3 has been replaced with the dialysis water. A n intended cleaning/disinfecting effect may not be obtained when the liquid chemical is introduced in the state in which the dialysate remains in the piping 3, but such a problem can be suppressed in the present embodiment.

In addition, since the concentration of the cleaning/disinfection liquid chemical can be detected by the sensors 4, whether the liquid chemical in the piping 3 has been replaced with the dialysis water can be detected at the time of post-cleaning by monitoring the detection values of the sensors 4. Therefore, the cleaning/disinfection control unit 82 in the present embodiment is configured to be able to detect whether the liquid chemical in the piping 3 has been replaced with the dialysis water at the time of the post-cleaning in Step S3, based on the detection result from at least one sensor 4. The cleaning/disinfection control unit 82 is configured to determine whether the inside of the piping 3 has been replaced with the dialysis water based on the detection result from the sensor 4, and finish the cleaning/disinfecting process when it is determined that the inside of the piping 3 has been replaced with the dialysis water. The liquid chemical comes into contact with patients blood in the next therapy and may adversely affect the blood purification therapy when the process is finished in the state in which the liquid chemical remains in the piping 3, but such a problem can be suppressed in the present embodiment.

Figure 3B:
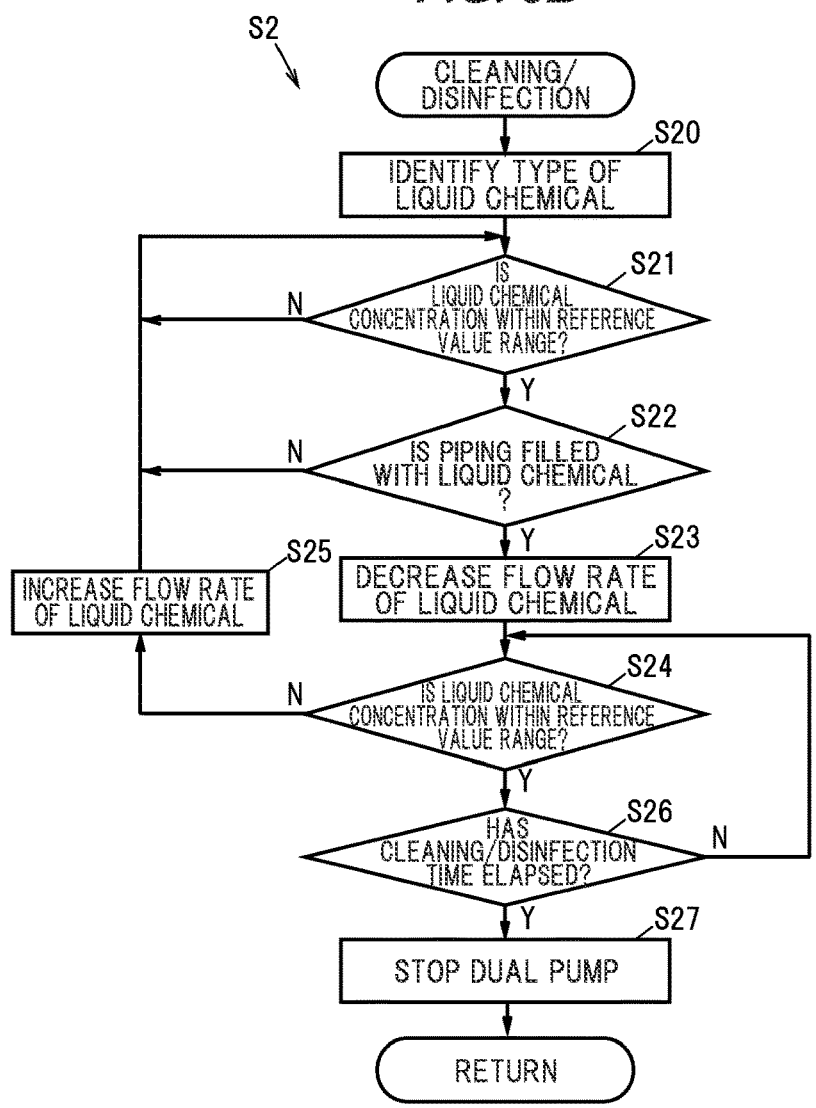
FIG. 3B is a flowchart of Step S2 in FIG. 3A.

As shown in FIG. 3B, in cleaning/disinfection in Step S2, firstly, the control unit 8 communicates with the dialysate supply device 11 and thereby acquires information indicating the liquid chemical used in the cleaning/disinfecting process from the dialysate supply device 11 in Step S20. Subsequently, the liquid chemical identification unit 81 specifies the liquid chemical based on the information indicating the liquid chemical and selects the sensor corresponding to the specified liquid chemical from the plural sensors 4.

After that, in Step S21, the liquid chemical identification unit 81 determines whether or not the concentration of the liquid chemical is within a predetermined reference value range by using the sensor 4 selected in Step S20. The liquid chemical identification unit 81 also identifies the type of the liquid chemical through the determination made in Step S21. That is, since the reference value range is set within a range in which the type of the liquid chemical can be identified, whether or not the type of the liquid chemical is appropriate in addition to whether or not the concentration of the liquid chemical is appropriate can be determined by determining whether or not the concentration of the liquid chemical is within the reference value range. Furthermore, although the information indicating the type of the liquid chemical is acquired and the type of the liquid chemical is specified in Step S20, it is possible to avoid cleaning/disinfection with an inappropriate type of liquid chemical even when a user puts a wrong type of liquid chemical instead of the liquid chemical which should be supplied and a liquid chemical of a different type from the controlled liquid chemical is sent from the dialysate supply device 11 due to the control since the type of the liquid chemical is identified in step S21.

When the determination made in Step S21 is NO, the process returns to Step S21 to repeat determination. When the determination made in Step S21 is YES, the liquid chemical replacement detection unit 821 detects whether the piping 3 is filled with the liquid chemical in Step S22. In particular, when a predetermined delay time has elapsed after the determination of YES is made in Step S21, the liquid chemical replacement detection unit 821 detects that the piping 3 is filled with the liquid chemical. When the determination made in Step S22 is NO, the process returns to Step S21.

When the determination made in Step S22 is YES, the liquid chemical flow rate control unit 822 reduces the flow rate of the liquid chemical by controlling the dual pump 5 in Step S23. After that, in Step S24, whether the concentration of the liquid chemical is within the reference value range is determined based on the detection result from the sensor 4. When the determination made in Step S24 is NO, the liquid chemical flow rate control unit 822 increases the flow rate of the liquid chemical by controlling the dual pump 5 in Step S25 and the process then returns to Step S21. Step S24 and Step S25 can be omitted in case that, e.g., the concentration of the liquid chemical is monitored by an external device and there is no risk of a decrease in the concentration of the liquid chemical.

When the determination made in Step S24 is YES, the cleaning/disinfection control unit 82 determines, in Step S26, whether a preset disinfection/cleaning time has elapsed after detecting that the piping 3 is filled with the liquid chemical in Step S22. When the determination made in Step S26 is NO, the process returns to Step S24.

When the determination made in Step S26 is YES, the cleaning/disinfection control unit 82 stops the flow of the liquid chemical by stopping the dual pump 5 in Step S27. After that, it returns (proceeding to Step S3 in FIG. 3A).

Modifications

In the present embodiment, the example in which the information indicating the liquid chemical to be used is acquired in advance from the dialysate supply device 11 has been described. However, this process (the process in Step S20 described above) may be omitted, and the liquid chemical may be identified by the plural sensors 4. In this case, preferably, all of the plural sensors 4 are used and the liquid chemical is identified based on the detection results from the plural sensors 4, instead of selecting the sensor to be used from the plural sensors 4 and identifying the liquid chemical based on the detection result from only this sensor.

Although the blood purification device 1 supplied with the dialysate or the cleaning/disinfection liquid chemical from the external dialysate supply device 11 has been described in the present embodiment, the blood purification device 1 may include a mechanism for preparing the dialysate or the cleaning/disinfection liquid chemical.

Alternatively, the blood purification device 1 may have a built-in tank, etc., for supplying the cleaning/disinfection liquid chemical or may be supplied with the cleaning/disinfection liquid chemical from a tank, etc., which is separately provided.

In addition, although the description is omitted in FIG. 3A, it is obviously possible to continuously perform cleaning/sterilization using different liquid chemicals such as, e.g., performing cleaning/sterilization using a disinfectant in a low oxidation after cleaning/sterilization using an acid cleaning solution. In this case, it is desirable to prevent mixing of the liquid chemicals by performing the pre-cleaning to replace the inside of the piping 3 with the dialysis water after finishing cleaning/sterilization with a given liquid chemical, and then performing cleaning/sterilization with another liquid chemical. This is because if different liquid chemicals are mixed, a toxic substance such as chlorine gas may be produced depending on a combination of the liquid chemicals. In such a case, the cleaning/disinfection control unit 82 should be configured to determine whether the inside of the piping 3 has been replaced with the dialysis water at the time of the cleaning step based on the detection result from the sensor 4, and proceed to cleaning/disinfection using the next liquid chemical when it is determined that the inside of the piping 3 has been replaced with the dialysis water. It is thereby possible to further suppress mixing of the liquid chemicals.

Furthermore, although it is detected that the piping 3 is filled with the liquid chemical based on the detection result from the sensor 4 in the present embodiment, it is not limited thereto. It is also possible to determine that the piping 3 is filled with the liquid chemical based on time elapsed since the start of liquid chemical supply. In this case, however, since the liquid chemical is not physically detected, reliability is slightly poor. That is, by determining whether the piping 3 is filled with the liquid chemical based on the detection result from the sensor 4 as in the present embodiment, it is possible to more accurately detect that the piping 3 is filled with the liquid chemical.

Functions and Effects of the Embodiment

As described above, the blood purification device 1 in the present embodiment is configured to be able to identify types of the liquid chemicals of at least not less than the number of the sensors 4 by using the plural sensors 4 of different detection types.

For example, in case of using one sensor, it is difficult to determine typical liquid chemicals used for the cleaning/disinfecting process. If, e.g., a very expensive and large-scale s equipment such as a spectrophotometer is used, it is possible to determine the liquid chemical by one equipment, but it is not realistic. When using plural sensors 4 of different detection types as in the present embodiment, it is possible to determine the typical liquid chemicals used for the cleaning/disinfecting process by using the sensors 4 which are relatively inexpensive and conventionally used for monitoring blood purification therapy. That is, in the present embodiment, it is possible to identify many types of cleaning/disinfection liquid chemicals with an inexpensive and simple system configuration and possible to perform an appropriate cleaning/disinfecting process according to the type of the liquid chemical.

Summary of the Embodiment

Technical ideas understood from the embodiment will be described below citing the reference numerals, etc., used for the embodiment. However, each reference numeral, etc., described below is not intended to limit the constituent elements in the claims to the members, etc., specifically described in the embodiment.

A blood purification device (1) for blood purification therapy performed through a blood purifier, the blood purification device (1) comprising: piping (3); a plurality of sensors (4) of different detection types that are provided on the piping (3); and a liquid chemical identification unit (81) that identifies a type of a cleaning/disinfection liquid chemical flowing through the piping (3) by using the plurality of sensors (4), wherein the liquid chemical identification unit (81) is configured to be able to identify types of the liquid chemicals of at least not less than the number of the plurality of sensors (4) by using the plurality of sensors (4).

The blood purification device described in [1], wherein the liquid chemical identification unit (81) selects all or part of the plurality of sensors (4) according to the type of the liquid chemical which should be used for cleaning/disinfection and, based on detection results from the selected all or part of sensors (4), identifies whether or not it is a liquid chemical which should be used for the cleaning/disinfection.

The blood purification device (1) described in [1] or [2], wherein the liquid chemical identification unit (81) is configured to be able to identify types of the liquid chemicals of more than the number of the plurality of sensors (4) based on a combination of the detection results from the plurality of sensors (4).

The blood purification device (1) described in any one of [1] to [3], comprising: a cleaning/disinfection control unit (82) to detect whether the piping (3) is filled with the cleaning/disinfection liquid chemical at the time of cleaning/disinfecting the piping (3), based on a detection result from at least one of the plurality of sensors (4).

The blood purification device (1) described in [4], wherein the cleaning/disinfection control unit (82) is configured to be able to detect whether a dialysate or the liquid chemical in the piping (3) has been replaced with dialysis water, based on a detection result from at least one of the plurality of sensors (4).

The blood purification device (1) described in any one of [1] to [5], wherein the plurality of sensors (4) comprise a conductivity sensor (4) to measure conductivity of a liquid flowing through the piping (3), and an absorbance sensor (42) to measure absorption of ultraviolet light by the liquid flowing through the piping (3).

The blood purification device (1) described in [6], wherein the liquid chemical identification unit (81) identifies the type of the liquid chemical by comparing a threshold for a detection value of the conductivity sensor (41) and a threshold for a detection value of the absorbance sensor (42), which are set for each type of the liquid chemical, with the detection values of the conductivity sensor (41) and the absorbance sensor (42).

Although the embodiment of the invention has been described, the invention according to claims is not to be limited the embodiment described above. In addition, not all combinations of the features described in the embodiment are necessary to solve the problem of the invention.

In addition, the invention can be appropriately modified and implemented without departing from the gist thereof. For example, although the example in which the liquid chemical flow rate control unit 822 is provided has been described in the embodiment, the liquid chemical flow rate control unit 822 can be omitted.

REFERENCE SIGNS LIST

1: blood purification device
3: piping
4: sensor
41: conductivity sensor
42: absorbance sensor
5: dual pump
8: control device
81: liquid chemical identification unit
82: cleaning/disinfection control unit
821: liquid chemical replacement detection unit
822: liquid chemical flow rate control unit

The invention claimed is:

1. A blood purification device for blood purification therapy performed through a blood purifier, the blood purification device comprising:
   piping;
   a plurality of sensors of different detection types that are provided on the piping, the plurality of sensors comprise:
      a conductivity sensor configured to measure conductivity of a liquid flowing through the piping, and
      an absorbance sensor to measure absorption of ultraviolet light by the liquid flowing through the piping; and
   a liquid chemical identification unit that identifies a type of a cleaning/disinfection liquid chemical flowing through the piping by using the plurality of sensors, wherein the liquid chemical identification unit is configured to be able to identify types of liquid chemicals of at least not less than a number of the plurality of sensors by using the plurality of sensors.

2. The blood purification device according to claim 1, wherein the liquid chemical identification unit selects all or part of the plurality of sensors according to the type of the liquid chemical which should be used for cleaning/disinfection and, based on detection results from the selected all or part of sensors, identifies whether or not it is a liquid chemical which should be used for the cleaning/disinfection.

3. The blood purification device according to claim 1, wherein the liquid chemical identification unit is configured to be able to identify types of the liquid chemicals of more than the number of the plurality of sensors based on a combination of detection results from the plurality of sensors.

4. The blood purification device according to claim 1, comprising:
   a cleaning/disinfection control unit to detect whether the piping is filled with the cleaning/disinfection liquid chemical at a time of cleaning/disinfecting the piping, based on a detection result from at least one of the plurality of sensors.

5. The blood purification device according to claim 4, wherein the cleaning/disinfection control unit is configured to be able to detect whether a dialysate or the liquid chemical in the piping has been replaced with dialysis water, based on a detection result from at least one of the plurality of sensors.

6. The blood purification device according to claim 1, wherein the liquid chemical identification unit identifies the type of the liquid chemical by comparing a threshold for a detection value of the conductivity sensor and a threshold for a detection value of the absorbance sensor, which are set for each type of the liquid chemical, with the detection values of the conductivity sensor and the absorbance sensor.

* * * * *